United States Patent [19]
Allen
[11] Patent Number: 4,809,687
[45] Date of Patent: Mar. 7, 1989

[54] MEDICAL STIRRUP

[75] Inventor: R. Daniel Allen, Newbury, Ohio
[73] Assignee: Edgewater Medical Systems, Mayfield Heights, Ohio

[21] Appl. No.: 139,572
[22] Filed: Dec. 30, 1987
[51] Int. Cl.[4] ..... A61F 5/04
[52] U.S. Cl. ..... 128/84 R; 128/80 R; 269/328
[58] Field of Search ..... 269/328; 128/80 R, 83, 128/84 R, 84 A, 84 B, 84 C, 87 R, 581, 586; 5/443, 444

[56] References Cited

U.S. PATENT DOCUMENTS

| | | | |
|---|---|---|---|
| 795,903 | 8/1905 | Foster | 269/328 |
| 1,011,150 | 12/1911 | Brennan | 269/328 |
| 2,057,992 | 10/1936 | Wiruth | 269/328 |
| 2,644,448 | 7/1953 | Jardine | 128/84 R |
| 2,792,266 | 5/1957 | Waters | 269/328 |
| 2,796,061 | 6/1957 | Miller | 128/84 R |
| 3,149,630 | 9/1964 | Schmidt | 128/84 R |
| 3,153,411 | 10/1964 | Unks | 128/84 R |
| 3,516,652 | 6/1970 | Roblee | 269/328 |
| 3,745,996 | 7/1973 | Rush, Sr. | 128/84 B |
| 3,957,041 | 5/1976 | Wilder | 128/94 |
| 3,982,742 | 9/1976 | Ford | 269/328 |
| 4,076,022 | 2/1978 | Walker | 128/892 |
| 4,186,738 | 2/1980 | Schleicher et al. | 128/892 |
| 4,407,277 | 10/1983 | Ellison | 128/82 |
| 4,446,856 | 5/1984 | Jordan | 128/80 R |
| 4,564,164 | 1/1986 | Allen et al. | 248/118 |

FOREIGN PATENT DOCUMENTS

| | | | |
|---|---|---|---|
| 3228753 | 2/1984 | Fed. Rep. of Germany | 128/80 R |
| 2375856 | 12/1976 | France | 128/80 R |
| 363452 | 10/1938 | Italy | 128/84 |
| 317583 | 11/1956 | Switzerland | 269/328 |

*Primary Examiner*—Robert A. Hafer
*Assistant Examiner*—Kevin G. Rooney
*Attorney, Agent, or Firm*—Pearne, Gordon, McCoy & Granger

[57] ABSTRACT

A medical stirrup for supporting a patient's limb in a desired attitude is disclosed. The limb is cradled in a shell lined with a soft material. The limb is retained in the shell by adjustable bands. The shell is suspended from a support by adjustable straps. The attitude of the limb is controlled by the adjustment of the straps and the positioning of the support.

10 Claims, 3 Drawing Sheets

MEDICAL STIRRUP

BACKGROUND OF THE INVENTION

This invention relates to an apparatus for supporting a patient's limb during medical procedures.

It is well-known in the art to suspend a patient's limb by a sling attached to a support, either a free-standing stand or a boom attached to an operating table. The boom and stand typically have the capability to telescope or slide through adjustable clamps to vary the limb's position depending on the patient's size or the procedure to be performed.

The sling is usually just one or more straps looped about the limb. The use of looped straps results in several problems. The limited support surface afforded by the straps produce significant points of pressure on the limb. In extreme cases, a tourniquet effect may result. Also, the fact that the limb is merely hung from the support, rather than being supported, places substantial strain on the joints involved. This is particularly critical if the joints are affected by degenerative disease or damaged from injuries.

In many surgical procedures, it is necessary to position a limb and joint in a particular attitude. Surgery on a joint often requires loading it in certain directions to provide optimum access to the interior of the joint. Prior art limb supports use complicated clamps, booms and restraints to position the limb in the desired attitude.

The medical stirrup disclosed herein provides improved support of limbs during medical procedures. Support is provided over a substantial portion of the limb, thereby avoiding pressure points and constrictions. In addition, the device allows easy manipulation of the attitude of the limb, making it possible to provide desired loading and orientation of particular joints.

The limb to be supported is cradled in a shell. The shell is shaped to conform to the underside of the limb to be supported. In the case of a leg support, the shell is shaped like an open-fronted boot. The shell is preferably cosntructed from an electrically nonconducting material, thereby helping to avoid undesired grounding of the patient. The inside of the shell is preferably provided with a cushioning lining of foam rubber. The lining further enhances the even spreading of pressure over the entire supported surface.

To read the limb within the shell, bands are attachable to opposite sides of the shell. One end of a band attaches to one side of the shell, the band passes over the limb and the other end of the band is attached to the opposite side of the shell. The band may be adjustable with buckles or hook-and-loop closures for example.

The shell is suspended from a support by adjustable straps. The straps are preferably attached to the edges of the shell at one of their ends, the other end being attachable to the support. The straps may be adjustable with buckles or other means well known in the art. By adjusting the length of the straps, the attitude of the limb can be adjusted to the desired position. This allows controlling the forces on different joints, either to minimize strain, or purposely load a joint to aid in the medical procedure. In addition, the limb can be located in positions convenient for access to other areas of the patient.

The support for suspending the shell may be either a free-standing stand or a boom attached to an operating table. The stand or the boom preferably has an inverted U-shaped top end to allow suspension of the shell by the straps from the end of the stand while maintaining clearance between the stand and the side of the shell. The free-standing stand preferably has a telescoping height adjustment and a base that may be positioned anywhere on the floor or similar surface. The boom is preferably attached to an operating table with a clamp that allows sliding adjustment of both length and position of the boom with respect to the patient.

More than one of the present stirrups may be advantageously employed in medical procedures requiring the support of more than one limb. For example, two boot-like embodiments of the stirrup may be used to support a patient's legs for gynecological, cystoscopic and lithotomy procedures.

SUMMARY OF THE INVENTION

A new and improved medical stirrup for suspending a patient's limb from a support is disclosed. The stirrup comprises a shell to provide broad support for the limb, several bands to hold the limb within the shell, and several adjustable straps attached to the shell for suspending the shell from the support. The straps are adjusted to suspend the limb in the desired attitude. A padded lining may be used to help cradle the limb. The shell is preferably made of plastic to provide electrical insulation of the patient. In the case of a leg support, the shell is shaped like an open front boot.

DESCRIPTION OF THE PREFERRED EMBODIMENT

Figure 1:
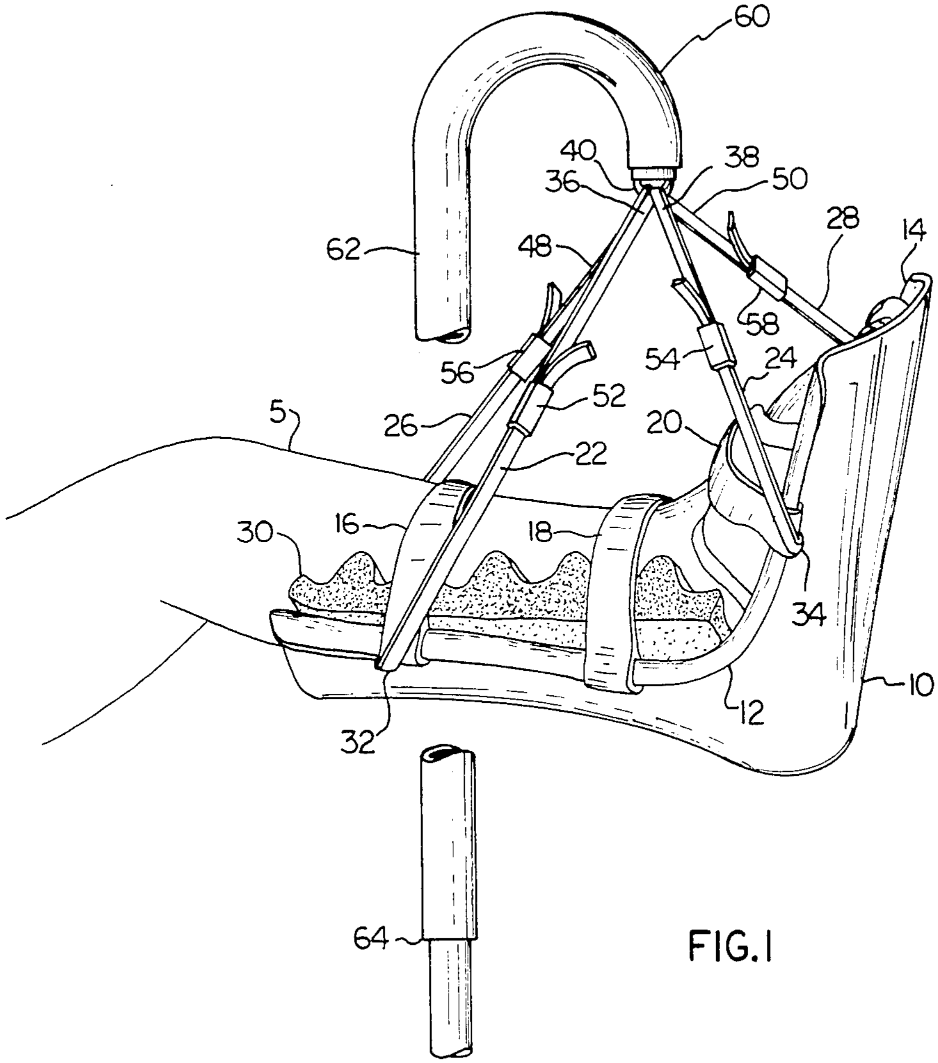
FIG. 1 is a partially cut away perspective view of a leg stirrup embodiment of the invention using a telescoping, free-standing agent for a support.

Referring to the drawings, a leg stirrup embodiment of the invention is shown in use with a patient's leg 5. The shell 10 is formed in the shape of a frontless boot. The shell should preferably support at least 10 inches of leg 5.

Rolled edges 12 and 14 are integrally formed at the sides of shell 10 and act to reenforce shel 10 as well as to provide convenient attachment points for bands 16, 18 and 20, and straps 22, 24, 26 and 28. Shell 10 is preferably made of rigid plastic for reasons of both economy and insulating the patient from inadvertent grounding during the use of electrocauterization and other procedures using electrical current.

Lining 30 is interposed between the patient's leg 5 and shell 10. The leg 5 is cushioned on lining 30, thereby evenly spreading the pressure from the weight of leg 5 as supported by shell 10. Lining 30 is preferably composed of foam rubber but may be of other soft materials.

Bands 16, 18 and 20 are attachable from edge 12 to edge 14 of shell 10 to retain leg 5 in shell 10. Band 16 is located in the calf area of shell 10, band 18 is located in the ankle area of shell 10, and band 20 is located in the foot area of shell 10. Hook-and-loop closures (not shown) on straps 16, 18 and 20 are used to adjust the length of bands 16, 18 and 20 to ensure snug retention of leg 5 in shell 10.

The lower ends 32 and 34, respectively, of straps 22 and 24 are attached to edge 12; and the upper ends 36 and 38, respectively, of straps 22 and 24 are attachable to eyelet 40. Similarly, the lower ends 44 and 46, respectively, of straps 26 and 28 are attached to edge 14; and the upper ends 48 and 50 are attachable to eyelet 40. Buckles 52, 54, 56, and 58 provide means to adjust the length of straps 22, 24, 26 and 28, respectively; and hence the attitude of leg 5.

Figure 3:
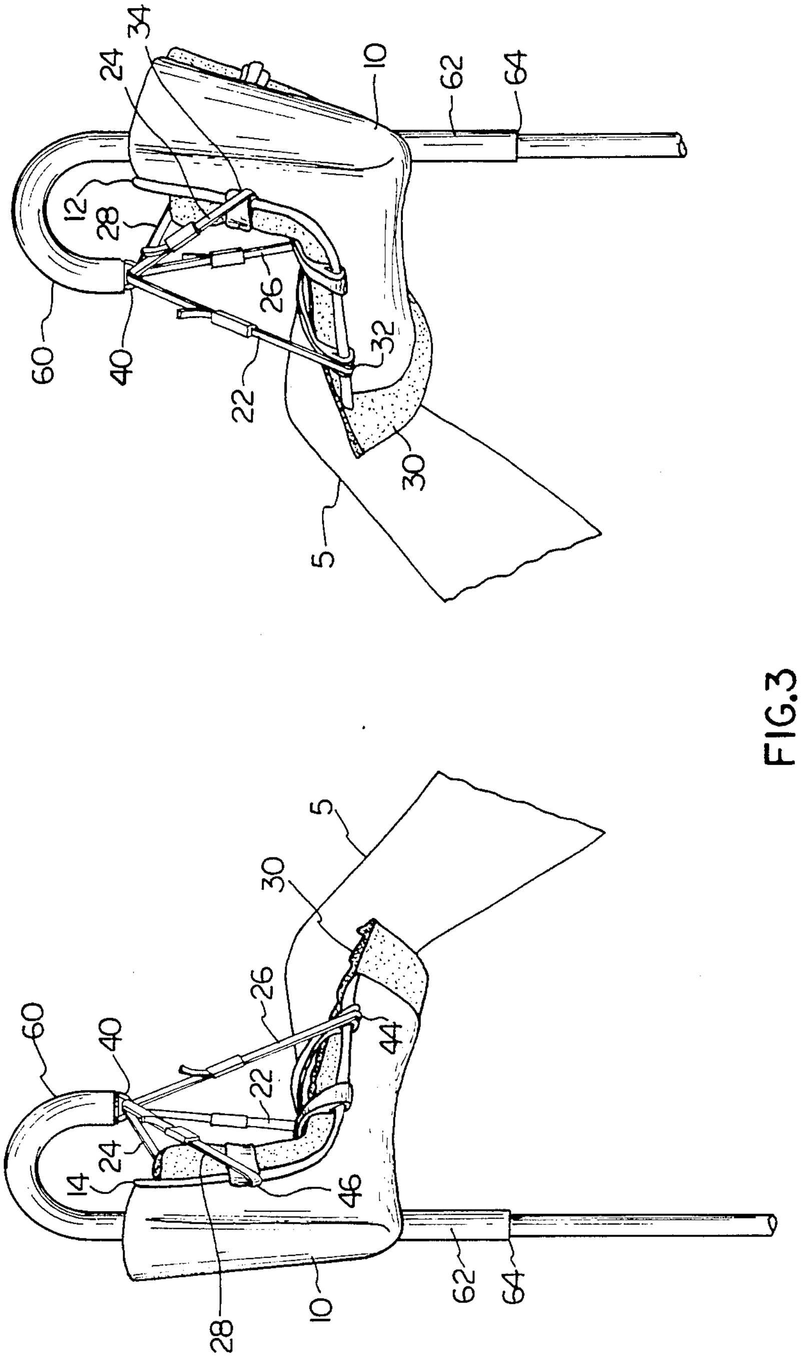
FIG. 3 shows two of the claimed devices employed to provide operative site access for cystoscopic procedures or procedures with similar access requirements.

In the embodiment of FIGS. 1 and 3, eyelet 40 is attached to U-shaped arm 60 formed in free-standing stand 62. Stand 62 is held in an upright position by an unshown base that may be positioned as desired on an operating room floor or similar surface. A telescoping joint 64 allows stand 62 to be adjusted for height.

In operation, leg 5 is securely held in shell 10 by firmly tightening bands 16, 18 and 20 about leg 5. Stand 62 is placed in the desired position on the floor and arm 60 is adjusted to the desired height using telescoping joint 64. Straps 22, 24, 26 and 28 are then attached to eyelet 40 on stand 62. Straps 22, 24, 26 and 28 are then adjusted in length, respectively, by buckles 52, 54, 56 and 58 to place the limb in the desired attitude. The interaction of the placement and height of the stand 62 with the adjustment of straps 22, 24, 26 and 28 allows not only the position of the limb to be adjusted, but also the loading of the joints involved because of the moments generated by shell 10 in conjunction with the weight of the limb.

Figure 2:
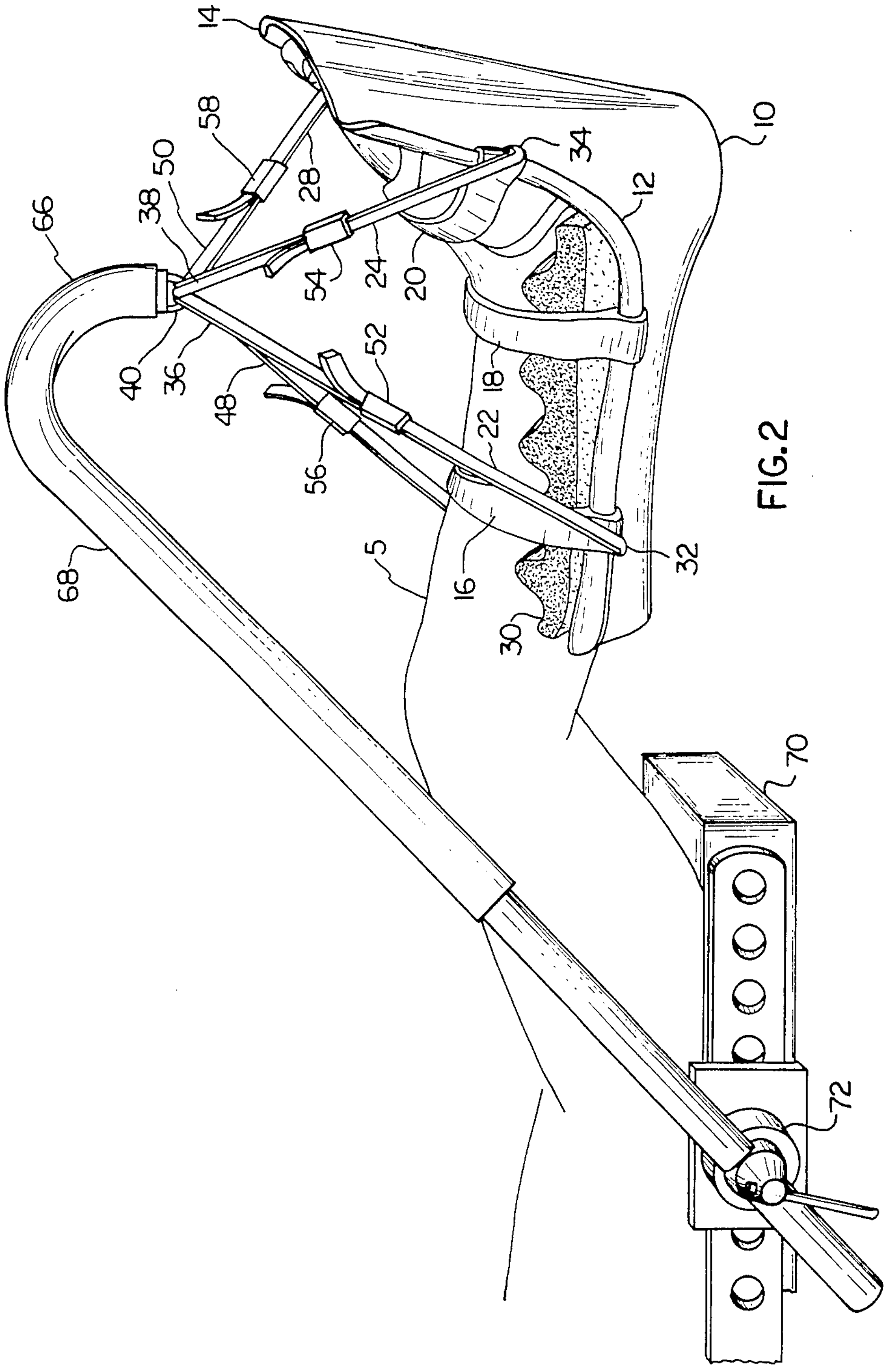
FIG. 2 is a perspective view of a leg stirrup embodiment of the invention using an adjustable boom attached to an operating table for a support.

In the embodiment of FIG. 2, eyelet 40 is attached to U-shaped arm 66 formed in boom 68. Boom 68 is mounted to operating table 70 by clamp 72. The orientation of boom 68 is determined by the position of clamp 72. Loosening clamp 72 allows both the angle and the extended length of boom 68 to be adjusted. Tightening clamp 72 retains boom 68 in the chosen position.

Operation of the embodiment of FIG. 2 is similar to that of FIG. 1, except that the position and height of eyelet 40 are set by the adjustment of boom 68 within clamp 72.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. A medical stirrup for suspending a patient's limb from a support, comprising:

(a) a rigid shell having a first portion that supports the bottom of a foot and a second portion that supports the rear part of a leg;

(b) a plurality of adjustable bands, said bands attachable to said shell to retain said limb cradlingly in said shell; and (c) a plurality of adjustable straps, said straps attached to either side of the first portion and either side of the second portion of said shell and connectable to said support for suspending said shell from said support, wherein said straps may be adjusted to maintain the limb in a desired altitude and angular position in order to adjust the loading on the joints of the patient's limb.

2. A stirrup as in claim 1, wherein said shell further comprises a cushioning lining.

3. A stirrup as in claim 1, wherein said shell is constructed of an electrically nonconducting material.

4. A stirrup as in claim 1, wherein said shell is bootlike and is of sufficient dimensions to provide substantial support of a patient's calf.

5. A medical stirrup for supporting a patient's limb, comprising:

(a) a support;

(b) a rigid shell having a first portion that supports the bottom of the foot and a second portion that supports the rear part of the leg;

(c) a plurality of adjustable bands, said bands attachable to said shell to retain said limb cradingly in said shell; and (d) a plurality of adjustable straps, said straps attached to either side of the first portion and either side of the second portion of said shell and connectable to said support for suspending said shell from said support, wherein said straps may be adjusted to maintain the limb in a desired altitude and angular position to adjust the loading on the joints of the patient's limb.

6. A stirrup as in claim 5, wherein said support is a free-standing, adjustable-height stand.

7. A stirrup as in claim 5, wherein said support is a boom, said boom adjustably attachable to an operating table.

8. A stirrup as in claim 5, wherein said shell further comprises a cushioning lining.

9. A stirrup as in claim 5, wherein said shell is constructed of an electrically nonconducting material.

10. A stirrup as in claim 5, wherein said shell is bootlike and is of sufficient dimensions to provide substantial support of a patient's calf.

* * * * *